(12) United States Patent
Kirkpatrick et al.

(10) Patent No.: US 9,585,393 B2
(45) Date of Patent: Mar. 7, 2017

(54) SAFLUFENACIL, FLUMIOXAZIN, AND 2,4-D WEED CONTROL COMPOSITIONS AND METHODS OF USE THEREOF

(71) Applicant: Valent U.S.A., Corporation, Walnut Creek, CA (US)

(72) Inventors: Matthew Terrence Kirkpatrick, Lathrop, MO (US); John Andrew Pawlak, II, Walnut Creek, CA (US)

(73) Assignee: Valent U.S.A., Corporation, Walnut Creek, CA (US)

( * ) Notice: Subject to any disclaimer, the term of this patent is extended or adjusted under 35 U.S.C. 154(b) by 0 days.

(21) Appl. No.: 14/638,203

(22) Filed: Mar. 4, 2015

(65) Prior Publication Data

US 2015/0250180 A1 Sep. 10, 2015

Related U.S. Application Data

(60) Provisional application No. 61/948,163, filed on Mar. 5, 2014.

(51) Int. Cl.
*A01N 43/54* (2006.01)
*A01N 43/84* (2006.01)
*A01N 39/04* (2006.01)

(52) U.S. Cl.
CPC ............. *A01N 43/84* (2013.01); *A01N 43/54* (2013.01)

(58) Field of Classification Search
CPC combination set(s) only.
See application file for complete search history.

(56) References Cited

U.S. PATENT DOCUMENTS

| 2013/0143742 A1 | 6/2013 | Ikeda | |
|---|---|---|---|
| 2013/0237417 A1 | 9/2013 | Ikeda | |
| 2015/0173363 A1* | 6/2015 | Ikeda | A01N 43/84 504/128 |

FOREIGN PATENT DOCUMENTS

| CN | 103271046 | | 9/2013 |
|---|---|---|---|
| JP | 2-32004 | * | 2/1990 |

OTHER PUBLICATIONS

Derwent abstract 1990-079173, abstracting JP 2-32004 (1990).*
JPO abstract JP402032004A, abstracting JP 2-32004 (1990).*
Tomlin, C.D.S., The Pesticide Manual, 15$^{th}$ ed., BCPC, pp. 294-300 (2009).*
Rao, V.S. Principles of Weed Science, Science Publishers, Inc., NH (USA), p. 352 (2000).*
International Search Report and Written Opinion issued by the International Bureau as PCT/US15/18654 on May 20, 2015.
Bruce et al., "Horseweed (*Conyza canadensis*) control in no-tillage soybeans (glycine max) with preplant and preemergence herbicides", Weed Technology, 1990, vol. 4, pp. 642-647.

* cited by examiner

*Primary Examiner* — John Pak
(74) *Attorney, Agent, or Firm* — Wood, Phillips, Katz, Clark & Mortimer

(57) ABSTRACT

The present invention is directed to compositions containing herbicidal mixtures comprising saflufenacil, flumioxazin, and 2,4-Dichlorophenoxyacetic, and methods of controlling weed growth with the composition. The mixtures of the present invention are especially effective on Horseweed (*Conyza Canadensis*) and grasses.

5 Claims, No Drawings

SAFLUFENACIL, FLUMIOXAZIN, AND 2,4-D WEED CONTROL COMPOSITIONS AND METHODS OF USE THEREOF

CROSS-REFERENCE TO RELATED APPLICATION

This application claims priority of U.S. Provisional Application 61/948,163 filed Mar. 5, 2014, the disclosure of which is incorporated herein by reference.

FIELD OF THE INVENTION

The present invention relates to agricultural compositions useful for killing weeds, and methods of use thereof.

BACKGROUND OF THE INVENTION

Unwanted plants, such as weeds, reduce the amount of resources available to crop plants and can have a negative effect on crop plant yield. Commonly unwanted plants in crop plant environments include broadleaf plants and grasses.

Herbicides are used to kill unwanted plants, such as weeds, in crop plant environments. Herbicides are expensive, and their use may result in unintentional consequences such as groundwater contamination, environmental damage, herbicide-resistant weeds, and human and mammalian health concerns. It is therefore desirable to minimize the amount of herbicides applied to a crop-growing environment or any area in need of weed control.

The herbicide saflufenacil, (N'-[2-chloro-4-fluoro-5-(3-methyl-2,6-dioxo-4-(trifluoromethyl)-3,6-dihydro-1(2H)-pyrimidinyl)benzyl]-N-isopropyl-N-methylsulfamide), is the active ingredient in the commercially available herbicide Sharpen® (available from BASF Chemical Company). Saflufenacil has some activity on horseweed and some activity on grasses at high concentrations, such as concentrations of at least 0.022 lb ai/acre. However, high rates of saflufenacil may damage crop plants. In addition, Sharpen®'s product label cautions that the product should not be applied on soybeans with herbicides such as sulfentrazone or flumioxazin as a tank mix or as a sequential application within 30 days of planting because crop injury may result.

The herbicide flumioxazin, (2-[7-fluoro-3,4-dihydro-3-oxo-4-(2-propynyl)-2H-1,4-benzoxazin-6-yl]-4,5,6,7-tetrahydro-1H-isoindole-1,3(2H)-dione), is the active ingredient in the commercially available herbicide Valor® (available from Valent USA Corporation). Valor® provides excellent broadleaf residual control of weeds such as Palmer amaranth and waterhemp. Valor® is also an excellent pre-emergence herbicide. However, flumioxazin has limited control on large Horseweed (*Conyza Canadensis*) and on growing grasses. Flumioxazin is not used as a post-emergence herbicide.

Herbicides such as flumioxazin and saflufenacil are protoporphyrinogen oxidase (PPO) inhibitors and use a membrane-disruption mechanism to destroy leaf tissue. PPO is an enzyme that naturally occurs in plants that is crucial to the formation of chlorophyll. When PPO inhibitors prevent PPO activity, singlet oxygen accumulates within plant cells and disrupts cell membranes.

The herbicide 2,4-Dichlorophenoxyacetic acid ("2,4-D") is a synthetic auxin plant hormone. 2,4-D causes stem curl-over, leaf withering, and eventual plant death by increasing the plants' growth to an unsustainable rate. 2,4-D is used for the control of broadleaf weeds, however, 2,4-D has limited activity on small Horseweed and no activity on grasses.

Unwanted plants, such as weeds, may greatly reduce yields of crop plants. For example, a Horseweed infestation reportedly was responsible for an 80% reduction in soybean yields. Bruce, J. A., and J. J. Kells, *Horseweed (Conyza Canadensis) control in no-tillage soybeans (Glycine max) with preplant and preemergence herbicides*, Weed Technol. 4:642-647 (1990). Therefore, controlling weeds, and especially grasses and Horseweed, is a major concern of crop growers.

Further, Horseweed and other grasses are becoming resistant to glyphosate. As early as 2000, glyphosate resistant Horseweed was reported in Delaware. Glyphosate resistant Horseweed has since been reported in numerous states. Accordingly, there is a need for new products that can provide effective kill rates of glyphosate resistant Horseweed.

No-till farming has been increasing in popularity because it has many benefits, including decreased labor time and decreased soil erosion. However, one of the downsides of no-till farming is that weeds are harder to control in these areas because they are not subjected to tilling. Accordingly, there is an increasing need for alternative ways to handle weed infestation.

In summary, there is a need for a composition that reduces the amount of herbicides necessary to obtain sufficient weed control while minimizing the harm to crop plants. As more weeds become resistant to herbicides, alternative compositions with high weed control are desired. Further, as no-till farming continues to increase in popularity, there is a greater need for effective herbicides. A composition with effective weed control and lower dosage rate will lead to increased crop plant yields, and decreased environmental, human, and mammalian health concerns.

SUMMARY OF THE INVENTION

In one aspect the invention is directed to agricultural compositions comprising an effective amount of saflufenacil, an effective amount of flumioxazin, and an effective amount of 2,4-D.

In another aspect, the invention is directed to methods for controlling weeds comprising applying a composition comprising an effective amount of saflufenacil, an effective amount of flumioxazin, and an effective amount of 2,4-D to an area in need of weed control.

DETAILED DESCRIPTION OF THE INVENTION

It was surprisingly discovered that combining saflufenacil with flumioxazin and 2,4-D allowed for more effective Horseweed and grass control when compared to application of each of the individual components of the composition or any combination of two components. It was unexpected that the combination of saflufenacil with flumioxazin and 2,4-D would result in better kill rates than twice the amount of saflufenacil alone. The synergy of the combination of saflufenacil, flumioxazin, and 2,4-D was also unexpected.

In one embodiment, the invention is directed to agricultural compositions comprising an effective amount of saflufenacil, an effective amount of flumioxazin, and an effective amount of 2,4-D. Preferably, the compositions of the present invention contain a ratio of saflufenacil to flumioxazin from about 1:1.5 to about 1:6 and a ratio of saflufenacil to 2,4-D from about 1:11 to about 1:50. In a more preferred embodiment, the compositions of the present invention contain a ratio of saflufenacil to flumioxazin from about 1:2 to about 1:6 and a ratio of saflufenacil to 2,4-D from about 1:15 to about 1:50. In a most preferred embodiment, compositions of the present invention contain a ratio of saflufenacil to flumioxazin of from about 1:3 to about 1:6 and a ratio of saflufenacil to 2,4-D from about 1:25 to about 1:50.

In another embodiment, the invention is directed to methods for controlling weeds comprising applying a composition comprising an effective amount of saflufenacil, an effective amount of flumioxazin, and an effective amount of 2,4-D to an area in need of weed control.

In further embodiment, the compositions of the present invention are applied to an area in need of post emergence weed control.

In yet another embodiment, the invention is directed to methods for controlling weeds wherein the weeds are Horseweed (*Conyza Canadensis*), Large Crabgrass (*Digitaria sanguinalis*), Palmer Amaranth (*Amaranthus palmeri*), Broadleaf Signalgrass (*Brachiaria platyhylla*), Common Barnyardgrass (*Echinochloa crus-galli*), Yellow Nutsedge (*Cyperus esculentus*), and Eclipta (*Eclipta prostrate*). In a preferred embodiment, the weed controlled is Horseweed.

In a preferred embodiment, the herbicides are applied concurrently or sequentially to the area in need of weed control.

In a further embodiment, the invention is directed to agricultural compositions comprising a synergistic amount of saflufenacil, flumioxazin, and 2,4-D.

In a preferred embodiment, the invention is directed to methods wherein the effective amount of saflufenacil is from about 0.01 to about 0.045 lb ai/acre. In a preferred embodiment, the amount of saflufenacil is from about 0.010 lb ai/acre to about 0.030 lb ai/acre, more preferably from about 0.011 lb ai/acre to about 0.025 lb ai/acre, and most preferably from about 0.017 lb ai/acre to about 0.023 lb ai/acre.

In a preferred embodiment, the invention is directed to methods wherein the effective amount of flumioxazin is from about 0.01 lb ai/acre to about 0.10 lb ai/acre. In a more preferred embodiment, the amount of flumioxazin is from about 0.04 lb ai/acre to about 0.07 lb ai/acre, more preferably from about 0.05 lb ai/acre to about 0.07 lb ai/acre. In another preferred embodiment, the amount of saflufenacil is about 0.064 lb ai/acre.

In a preferred embodiment, the invention is directed to methods wherein the effective amount of 2,4-D is from about 0.1 lb ai/acre to about 1.0 lb ai/acre. In a more preferred embodiment, the amount of 2,4-D is from about 0.2 lb ai/acre to about 0.9 lb ai/acre, more preferably from about 0.25 lb ai/acre to about 0.6 lb ai/acre. In another preferred embodiment, the amount of 2,4-D is preferably from about 0.45 lb ai/acre to about 0.55 lb ai/acre, and most preferred at about 0.5 lb ai/acre.

Preferably, the synergistic compositions of the present invention contain a ratio of saflufenacil to flumioxazin from about 1:1.5 to about 1:6 and a ratio of saflufenacil to 2,4-D from about 1:11 to about 1:50. In a more preferred embodiment, the compositions of the present invention contain a ratio of saflufenacil to flumioxazin from about 1:2 to about 1:6 and a ratio of saflufenacil to 2,4-D from about 1:15 to about 1:50. In a most preferred embodiment, compositions of the present invention contain a ratio of saflufenacil to flumioxazin of from about 1:3 to about 1:6 and a ratio of saflufenacil to 2,4-D from about 1:25 to about 1:50.

Applicants' mixtures can be applied by any convenient means. Those skilled in the art are familiar with the modes of application that include foliar applications such as spraying, chemigation (a process of applying the mixture through the irrigation system), by granular application, or by impregnating the mixture on fertilizer.

Applicants' mixtures can be prepared as concentrate formulations or as ready-to-use formulations.

The term "effective amount" means the amount of the formulation that will kill a weed. The "effective amount" will vary depending on the formulation concentration, the type of plants(s) being treated, the severity of the weed infestation, the result desired, and the life stage of the weeds during treatment, among other factors. Thus, it is not always possible to specify an exact "effective amount." However, an appropriate "effective amount" in any individual case may be determined by one of ordinary skill in the art.

The herbicide mixtures of the present invention may be formulated to contain adjuvants, such as solvents, anti-caking agents, stabilizers, defoamers, slip agents, humectants, dispersants, wetting agents, thickening agents, emulsifiers, and preservatives which increase the long lasting activity of the actives. Other components that enhance the biological activity of these ingredients may optionally be included.

Methylated seed oil ("MSO") is an adjuvant that improves leaf cuticle penetration of an agricultural active, such as a plant growth regulator, fungicide or herbicide. MSO can be used in the mixtures of the present invention, but is not required or responsible for the synergy of the combination of saflufenacil, flumioxazin, and 2,4-D. Other oil based adjuvants with similar qualities could also be used, such as crop oil concentrates.

Mixtures of the present invention can be formulated to contain a liquid solvent. Examples of solvents include water or oil concentrates.

Applicants' mixtures can also include one or more additional herbicides.

The mixtures of the present invention can be applied to any environment in need of weed control. The environment in need of weed control may include any area that is desired to have a reduced number of weeds or to be free of weeds. For example, the herbicide combination can be applied to an area used to grow crop plants, such as a field, orchard, or vineyard. For example, Applicants' compositions and methods can be applied to areas where soybeans, corn, peanuts, and cotton are growing. In a preferred embodiment, the mixture is applied in an area where a broadleaf crop (soybean, cotton, peanut, orchard, vineyard, forages) is growing. The mixtures of the present invention can also be applied to non-agricultural areas in need of weed control such as a lawns, golf courses, or parks.

Applicants' compositions and methods can be applied successfully to crop plants and weeds that are resistant to glyphosate. The composition and methods can also be applied to areas where genetically modified crops ("GMOs") or non-GMO crops are growing. The term "GMO crops" as used herein refers to crops that are genetically modified.

When used in this application, Horseweed refers to *Conyza Canadensis*, Large Crabgrass refers to *Digitaria sanguinalis*, Palmer Amaranth refers to *Amaranthus palmeri*, Broadleaf Signalgrass refers to *Brachiaria platyhylla*, Common Barnyardgrass refers to *Echinochloa crus-galli*, Yellow Nutsedge refers to *Cyperus esculentus*, Eclipta refers to *Eclipta prostrata*. Although the composition of the present invention has proven synergy when applied to Horseweed and grasses, the synergistic composition could be applied to any number of other weeds or undesired plants for effective control and is not limited to the examples. These could include Giant Ragweed (*Ambrosia trifida*), Common Ragweed (*Ambrosia artemisiifolia*), and Velvetleaf (*Abutilon theophrasti*).

Throughout the application, the singular forms "a," "an," and "the" include plural reference unless the context clearly dictates otherwise.

As used herein, "lb ai/acre" is an abbreviation for pounds of active ingredient per acre.

As used herein, all numerical values relating to amounts, weight percentages and the like are defined as "about" or "approximately" each particular value, plus or minus 10%. For example, the phrase "at least 5.0% by weight" is to be understood as "at least 4.5% to 5.5% by weight." Therefore, amounts within 10% of the claimed values are encompassed by the scope of the claims.

As used herein, "post emergence" refers to an herbicide treatment that is applied to an area after the weeds have germinated and emerged from the ground or growing medium.

As used herein, synergy means that when combined, the claimed composition achieves a result that is greater than the expected result.

These representative embodiments are in no way limiting and are described solely to illustrate some aspects of the invention.

Further, the following example is offered by way of illustration only and not by way of limitation.

EXAMPLE

Example 1

The following field test was conducted during spring in Mississippi. Sharpen® was used in the test as the source of saflufenacil. Valor® was used in the test as the source of flumioxazin. Roundup Ready soybeans (*Glycine max*) were used in the test as the crop plant. All of the treatments contained MSO concentrate oil at 1% v/v.

When the test began, the test plot had Horseweed that was 6 to 20 inches tall. Applications were administered at the concentrations as follows. Saflufenacil was administered at 0.011, 0.017 or 0.022 lb ai/acre (indicated in the table as "S" followed by the amount). Flumioxazin was administered at 0.064 lb ai/acre, and 2,4-D was administered at 0.5 lb ai/acre throughout the experiment. Three days after the treatment (3 DAT), soybeans were planted across the front of the plot. On 7 DAT, another pass of soybeans was planted across the front of the plot with a 30 inch planter. Each test was On 11 DAT, readings were taken to determine the survival of Horseweed and Crabgrass. On 12 DAT, readings were taken to determine the survival of Palmer Amaranth, Broadleaf Signalgrass, Common Barnyardgrass, Yellow Nutsedge, and *Eclipta*. Survival ratings were taken by counting the number of alive and dead plants at the time of the reading. The pytotoxicity of each treatment was also evaluated by examining the soybeans at 11 and 12 DAT. All data was analyzed using Bartlett's test and with p value of 0.5 for determining significance of the results. The results of this study can be seen below in "Table 1. The Effect of Saflufenacil, Flumioxazin and 2,4-D on Weeds."

TABLE 1

The Effect of Saflufenacil, Flumioxazin and 2,4-D on Weeds

| Treatments | Horseweed | Large Crabgrass | Palmer Amaranth | Broadleaf Signalgrass | Common Barnyardgrass | Yellow Nutsedge | Eclipta |
|---|---|---|---|---|---|---|---|
| Untreated Control | 0 | 0 | 0 | 0 | 0 | 0 | 0 |
| S 0.011 | 66.7 | 43.3 | 91.0 | 31.7 | 31.7 | 23.3 | 83.0 |
| S 0.017 | 78.3 | 60.0 | 91.3 | 45.0 | 41.7 | 35.0 | 91.3 |
| S 0.022 | 86.7 | 56.7 | 96.0 | 31.7 | 25.0 | 30.0 | 93.0 |
| Flumioxazin | 15.0 | 70.0 | 96.0 | 45.0 | 45.0 | 42.5 | 86.3 |
| Flumioxazin S 0.011 | 61.7 | 73.3 | 99.0 | 54.3 | 46.0 | 51.7 | 92.0 |
| Flumioxazin S 0.017 | 85.0 | 81.7 | 97.7 | 58.3 | 54.3 | 25.0 | 96.3 |
| Flumioxazin S 0.022 | 87.7 | 84.0 | 99.0 | 62.7 | 62.7 | 36.7 | 94.7 |
| 2,4-D | 11.7 | 50.0 | 91.0 | 21.7 | 15.0 | 8.3 | 91.0 |
| Flumioxazin 2,4-D | 35.0 | 70.0 | 99.0 | 66.2 | 63.3 | 35.0 | 93.0 |
| 2,4-D S 0.011 | 73.3 | 78.3 | 99.0 | 51.0 | 46.0 | 45.0 | 91.7 |
| 2,4-D S 0.017 | 75.0 | 79.3 | 99.0 | 66.0 | 63.3 | 58.3 | 97.7 |
| 2,4-D S 0.022 | 95.3 | 90.0 | 97.0 | 75.0 | 68.3 | 51.0 | 96.3 |
| 2,4-D Flumioxazin S 0.011 | 95.3 | 96.3 | 99.0 | 97.0 | 96.3 | 97.0 | 99.0 |
| 2,4-D Flumioxazin S 0.017 | 94.7 | 94.7 | 99.0 | 98.3 | 96.3 | 94.3 | 99.0 |
| 2,4-D Flumioxazin S 0.022 | 95.7 | 96.3 | 99.0 | 94.7 | 95.7 | 95.0 | 99.0 |

The results illustrate that a composition of saflufenacil, flumioxazin, and 2,4-D is synergistic as it allows for a lower application of saflufenacil while achieving effective kill rates. The combination of 0.011 lb ai/acre saflufenacil, 0.064 lb ai/acre flumioxazin, and 0.5 lb ai/acre 2,4-D had a better kill rate than saflufenacil alone, or saflufenacil with flumioxazin, saflufenacil with 2,4-D, or flumioxazin with 2,4-D.

Further, the three component mixture treatments allowed for less total amount of herbicide to be applied to the area in need of weed control, by reducing the total rate required of any single or two-way mixture to obtain an equivalent amount of weed control.

Applicants used the widely accepted fraction method for determining synergy. The fraction method involves not merely adding together the individual control percentages together, as that will often be greater than 100%. The fraction method involves taking the control as a decimal value (X), multiplying the 1 minus X values together, then taking the "1 minus" value to get the calculated control as a decimal value. For example, if two products give 60% control, the additive or predicted value would be 84% and not 120%. See Rao, V. S., *Principles of Weed Science*, Second Edition, (2000) 351-352, and the illustrative example below.

Example Calculation

| Component | % Control | Response as decimal | (1-response) |
|---|---|---|---|
| A | 60.00 | 0.6000 | 0.4000 |
| B | 60.00 | 0.6000 | 0.4000 | is multiplication of (1-0.1600 Response).
0.8400 is calculated additive control.

| A + B Calc Additive= | 84.00 | % Control |
|---|---|---|
| A + B Actual= | 95.30 | % Control |

When the fraction method is applied to Applicants' data, it reveals evidence of synergy. The chart below shows the calculations of the theoretical additive control and compares it to the actual control of the combination. As seen below, the predicted additive control was about 75%. In contrast, Applicants unexpectedly found that the 3-way combination provided a control of 95%.

Synergy Calculation

| % Alone | X = decimal | Y = (1 − X) |
|---|---|---|
| 67.00 | 0.6700 | 0.3300 |
| 12.00 | 0.1200 | 0.8800 |
| 15.00 | 0.1500 | 0.8500 |

A Saflufenacil
B 2,4-D
C Flumioxazin
is
0.2468 (YA*YB*YC)
is 1-0.7532 (YA*YB*YC)

| Calc Additive= | 75.32 | % Control |
|---|---|---|
| Actual= | 95.00 | % Control |

Applicants found that each component of the 3-way combination contributed to the synergy. For example, when saflufenacil was applied to Horseweed alone, it provided 67% control. Flumioxazin with 2,4-D provided 35% control. Saflufenacil should have only increased the control from 35% to 78% if the combination was simply additive. The actual increase was to 95%, significantly higher, which is evidence of synergy.

Similarly, 2,4-D alone provided a 12% control and saflufenacil with flumioxazin provided a 62% control. 2,4-D should have only increased the control from 62% to 66% if the combination was simply additive. The actual increase was to 95%, significantly higher, which is evidence of synergy.

Finally, flumioxazin alone provided a 15% control and 2,4-D with saflufenacil provided a 73% control. Flumioxazin should have only increased the control from 73% to 77% if the combination was simply additive. The actual increase was to 95%, significantly higher, which is evidence of synergy. The evidence of synergy was consistent among all three replications, as well.

Applicants also found that their 3-way combination resulted in a statistically significant different as determined by Bartlett's test and with p value of 0.5 for determining significance of the results.

Further, Applicants found that the treatments were non-phytotoxic to the crop plant soybeans. This finding allows for the treatments to be applied to areas where crop plants are growing that are in need of weed control.

What is claimed is:

1. An agricultural composition comprising a synergistically effective amount of saflufenacil, flumioxazin, and 2,4-dichlorophenoxyacetic acid (2,4-D), wherein the weight ratio of saflufenacil to flumioxazin is from about 1:3 to about 1:6, the weight ratio of saflufenacil to 2,4-D is from about 1:20 to about 1:50, and said amounts and ratios are effective to provide synergistic control of yellow nutsedge or common barnyardgrass compared to the additive control of same amount of saflufenacil alone and same amount of combination of flumioxazin and 2,4-D.

2. A method of controlling yellow nutsedge (*Cyperus esculentus*) or common barnyardgrass (*Echinochloa crus-galli*) comprising applying a synergistically effective amount of saflufenacil, flumioxazin, and 2,4-dichlorophenoxyacetic acid (2,4-D) to an area in need of yellow nutsedge or common barnyardgrass control, wherein the weight ratio of saflufenacil to flumioxazin is from about 1:3 to about 1:6, the weight ratio of saflufenacil to 2,4-D is from about 1:20 to about 1:50, and said amounts and ratios are effective to provide synergistic control of yellow nutsedge or common barnyardgrass compared to the additive control of same amount of saflufenacil alone and same amount of combination of flumioxazin and 2,4-D.

3. The method of claim 2 wherein the effective amount of saflufenacil is from about 0.010 to about 0.030 lb ai/acre, the effective amount of flumioxazin is from about 0.04 to about 0.07 lb ai/acre, and the effective amount of 2,4-D is from about 0.2 to about 0.6 lb ai/acre.

4. The composition of claim 3 wherein the effective amount of saflufenacil is from about 0.011 to about 0.023 lb ai/acre, the effective amount of flumioxazin is from about 0.05 to about 0.07 lb ai/acre, and the effective amount of 2,4-D is from about 0.4 to about 0.6 lb ai/acre.

5. The method of claim 2 wherein the saflufenacil, flumioxazin, and 2,4-D are applied concurrently or sequentially to the area in need of yellow nutsedge or common barnyardgrass control.

\* \* \* \* \*